United States Patent
Kanou et al.

(10) Patent No.: US 9,370,571 B2
(45) Date of Patent: Jun. 21, 2016

(54) AQUEOUS ACRYLAMIDE SOLUTION, STABILIZER FOR AQUEOUS ACRYLAMIDE SOLUTION, AND STABILIZATION METHOD FOR AQUEOUS ACRYLAMIDE SOLUTION

(75) Inventors: Makoto Kanou, Yokohama (JP); Norifumi Hagiya, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 210 days.

(21) Appl. No.: 14/118,008

(22) PCT Filed: May 21, 2012

(86) PCT No.: PCT/JP2012/062932
§ 371 (c)(1),
(2), (4) Date: Nov. 15, 2013

(87) PCT Pub. No.: WO2012/157776
PCT Pub. Date: Nov. 22, 2012

(65) Prior Publication Data
US 2014/0080914 A1  Mar. 20, 2014

(30) Foreign Application Priority Data
May 19, 2011 (JP) .................. 2011-112430

(51) Int. Cl.
| | | |
|---|---|---|
| A61K 47/22 | (2006.01) | |
| A61K 31/16 | (2006.01) | |
| A61K 47/02 | (2006.01) | |
| C07C 231/22 | (2006.01) | |
| C07C 233/09 | (2006.01) | |
| C12P 13/02 | (2006.01) | |
| C07D 211/94 | (2006.01) | |

(52) U.S. Cl.
CPC ................ *A61K 47/22* (2013.01); *A61K 31/16* (2013.01); *A61K 47/02* (2013.01); *C07C 231/22* (2013.01); *C07C 233/09* (2013.01); *C07D 211/94* (2013.01); *C12P 13/02* (2013.01)

(58) Field of Classification Search
CPC ....... A61K 31/16; A61K 47/02; A61K 47/22; C07C 231/22; C07C 233/09; C07D 211/94; C12P 13/02
See application file for complete search history.

(56) References Cited

U.S. PATENT DOCUMENTS

| | | | |
|---|---|---|---|
| 3,329,715 A | | 7/1967 | Strohmeyer et al. |
| 3,887,425 A | * | 6/1975 | Munch ........................ 159/48.2 |
| 4,248,968 A | | 2/1981 | Watanabe et al. |
| 4,637,982 A | | 1/1987 | Yamada et al. |
| 5,352,828 A | | 10/1994 | Seki et al. |
| 5,504,243 A | | 4/1996 | Sakamoto et al. |
| 6,835,288 B1 | * | 12/2004 | Sutoris et al. ..................... 203/3 |
| 2006/0024747 A1 | * | 2/2006 | Payne et al. .................... 435/7.1 |
| 2011/0021819 A1 | | 1/2011 | Kanou et al. |
| 2011/0160484 A1 | | 6/2011 | Fruchey et al. |

FOREIGN PATENT DOCUMENTS

| | | |
|---|---|---|
| EP | 0685447 | * 12/1995 |
| JP | 39 10109 | 6/1964 |
| JP | 40 7171 | 4/1965 |
| JP | 40 7172 | 4/1965 |
| JP | 41 1773 | 2/1966 |
| JP | 41 1930 | 2/1966 |
| JP | 45 011284 | 4/1970 |
| JP | 48 3818 | 2/1973 |
| JP | 50 14623 | 2/1975 |
| JP | 56 17918 | 4/1981 |
| JP | 59 37951 | 9/1984 |
| JP | 2 470 | 1/1990 |
| JP | 6 92919 | 4/1994 |
| JP | 8 48650 | 2/1996 |
| JP | 2548051 | 10/1996 |
| JP | 2010 537991 | 12/2010 |
| WO | 2009 113654 | 9/2009 |

OTHER PUBLICATIONS

International Search Report Issued Aug. 7, 2012 in PCT/JP12/062932 Filed May 21, 2012.

* cited by examiner

*Primary Examiner* — Paul A Zucker
*Assistant Examiner* — Mark Luderer
(74) *Attorney, Agent, or Firm* — Oblon, McClelland, Maier & Neustadt, L.L.P

(57) ABSTRACT

There is provided an aqueous acrylamide solution including 2,2,6,6-tetramethylpiperidine 1-oxyl in the ratio of 2 to 100 mg and manganese ions in the ratio of 0.2 to 2.0 mg per 1 kg of acrylamide. According to the present invention, an aqueous acrylamide solution having favorable quality and high stability with suppressed polymerization of acrylamide, a stabilizer used therefore, and a stabilization method can be provided.

18 Claims, No Drawings

US 9,370,571 B2

AQUEOUS ACRYLAMIDE SOLUTION, STABILIZER FOR AQUEOUS ACRYLAMIDE SOLUTION, AND STABILIZATION METHOD FOR AQUEOUS ACRYLAMIDE SOLUTION

TECHNICAL FIELD

The present invention relates to an aqueous acrylamide solution, a stabilizer for the aqueous acrylamide solution, and a method for stabilization of the aqueous acrylamide solution.

The present application claims priority to Japanese Patent Application No. 2011-112430, which has been filed in Japan on May 19, 2011, which is hereby incorporated by reference in its entirety.

Acrylamide has many applications, such as flocculating agents, petroleum recovering agents, paper strength enhancers in the paper producing industry, and thickeners for papermaking, and is a useful substance as a raw material for polymers.

Among industrial processes for acrylamide production, used long time ago is a sulfuric acid hydrolysis process which consists of the step of heating acrylonitrile together with sulfuric acid and water to obtain an aqueous solution of acrylamide sulfate salts. This process has then been replaced with a copper-catalyzed process in which acrylonitrile is reacted with water in the presence of a copper catalyst (for example, metal copper, reduced copper, Raney copper, or the like) to obtain an aqueous solution of acrylamide. In addition, in recent years, as a production process with fewer by-products, industrial production based on a biocatalyst method is also carried out as a biocatalyst method for obtaining an aqueous solution of acrylamide by using a biocatalyst such as nitrile hydratase derived from microorganisms (for example, Patent Documents 1 to 5).

As in the case of many unsaturated monomers, acrylamide is easy to polymerize by the action of light or heat and also has a property of very easily polymerizing particularly upon contact with the surface of iron, so that an aqueous solution of acrylamide has been difficult to stably handle since the polymerization of acrylamide easily occurs during each step of its production or during its preservation.

A method of using various stabilizers has been proposed as a method for stabilization by suppressing polymerization of acrylamide. Examples of the stabilizers include thiourea, ammonium rhodanide, nitrobenzol (Patent Document 6), ferron (Patent Document 7), furil dioxime (Patent Document 8), cyanide complex compound of chromium (Patent Document 9), p-nitrosodiphenyl hydroxyamine (Patent Document 10), and so on. Those stabilizers are used for preventing polymerization during a process of producing acrylamide or for stabilization of an aqueous solution of acrylamide.

CITATION LIST

Patent Document

Patent Document 1: JP 56-17918 B
Patent Document 2: JP 59-37951 B
Patent Document 3: JP 02-470 A
Patent Document 4: WO 2009/113654 A
Patent Document 5: JP 2548051 B1
Patent Document 6: JP 39-10109 B
Patent Document 7: JP 40-7171 B
Patent Document 8: JP 40-7172 B
Patent Document 9: JP 41-1773 B
Patent Document 10: JP 45-11284 B

DISCLOSURE OF THE INVENTION

Problem to be Solved by the Invention

The stabilizers described above all correspond to polymerization inhibitors. Stabilizers with a small stabilizing effect, that is, polymerization inhibiting effect, have problems of reduced quality of acrylamide, such as discoloration and reduced purity of acrylamide, because they should be added in large amounts to acrylamide. On the other hand, stabilizers with a high polymerization inhibiting effect may adversely affect the polymerization operations during production of acrylamide polymers such as having a difficulty to obtain desired high molecular weight polymers or reduced polymerization rate, even when used in small amounts.

The present invention is devised in view of the above circumstances, and an object of the present invention is to provide an aqueous acrylamide solution having favorable quality and high stability with suppressed acrylamide polymerization, a stabilizer used therefore, and a method for stabilization.

Means for Solving Problem

As a result of intensive studies to solve the problems stated above, the inventors of the present invention have found that, when 2,2,6,6-tetramethylpiperidine 1-oxyl (hereinbelow, described as TEMPO), which is one type of free radical, and manganese ions are included in an aqueous acrylamide solution, polymerization of acrylamide during its production and storage can be suppressed without having an adverse effect on the quality of acrylamide to thereby significantly improve its stability, and the present invention is completed accordingly.

The present invention has following aspects.

[1] An aqueous acrylamide solution containing TEMPO in the ratio of 2 to 100 mg/kg and manganese ions in the ratio of 0.2 to 2.0 mg/kg relative to acrylamide,

[2] The aqueous acrylamide solution described in [1], in which the acrylamide is produced by a reaction of acrylonitrile with water in the presence of a biocatalyst,

[3] The aqueous acrylamide solution described in [1] or [2], in which concentration of the acrylamide is 30 to 60% by mass,

[4] A stabilizer for aqueous acrylamide solution containing TEMPO and manganese ions, and

[5] A method for stabilization of an aqueous acrylamide solution including having, in an aqueous acrylamide solution, TEMPO in the ratio of 2 to 100 mg/kg and manganese ions in the ratio of 0.2 to 2.0 mg/kg relative to acrylamide.

Specifically, the present invention relates to the followings.

[1] An aqueous acrylamide solution containing 2,2,6,6-tetramethylpiperidine 1-oxyl in the ratio of 2 to 100 mg and manganese ions in the ratio of 0.2 to 2.0 mg relative to 1 kg of acrylamide,

[2] The aqueous acrylamide solution described in [1], in which the acrylamide is produced by a reaction of a composition containing acrylonitrile with water in the presence of a biocatalyst,

[3] The aqueous acrylamide solution described in [1] or [2], in which concentration of the acrylamide in the aqueous acrylamide solution is 30 to 60% by mass relative to the total weight of the aqueous acrylamide solution,

[4] A stabilizer for aqueous acrylamide solution containing 2,2,6,6-tetramethylpiperidine 1-oxyl and manganese ions,

[5] A method for stabilization of an aqueous acrylamide solution including having, in an aqueous acrylamide solution, 2,2,6,6-tetramethylpiperidine 1-oxyl in the ratio of 2 to 100 mg and manganese ions in the ratio of 0.2 to 2.0 mg relative to 1 kg of acrylamide, and

[6] Use of a composition containing 2,2,6,6-tetramethylpiperidine 1-oxyl and manganese ions for stabilization of an aqueous acrylamide solution.

Effect of the Invention

According to the present invention, an aqueous acrylamide solution having favorable quality and high stability with suppressed acrylamide polymerization, a stabilizer used therefore, and a method for stabilization can be provided.

BEST MODE(S) FOR CARRYING OUT THE INVENTION

Hereinafter, embodiments of the present invention will be described. The following embodiments are merely examples provided for illustrating the present invention, and the present invention is not intended to be limited thereto. The present invention may be carried out in various embodiments without departing from the spirit of the present invention.

All publications cited in this specification, including technical literatures, patent laid-open publications, patent publications and other patent documents, are incorporated herein by reference in their entirety.

<Aqueous Acrylamide Solution>

The aqueous acrylamide solution of the present invention contains TEMPO and manganese ions, each at predetermined ratio relative to acrylamide. In an aqueous acrylamide solution of a related art, TEMPO and manganese ions are not contained. By adding TEMPO and manganese ions to have a predetermined concentration, polymerization of acrylamide can be suppressed without lowering quality of aqueous acrylamide solution or having an adverse effect on process for polymerization. Accordingly, the aqueous acrylamide solution of the present invention has excellent stability.

Content of TEMPO is 2 to 100 mg, and preferably 5 to 50 mg relative to 1 kg of acrylamide.

Content of manganese ions is 0.2 to 2.0 mg, and preferably 0.4 to 1.2 mg relative to 1 kg of acrylamide.

When the content of TEMPO and content of manganese ions are less than 2 mg and less than 0.2 mg, respectively, per 1 kg of acrylamide, the stabilizing effect of suppressing acrylamide polymerization is small. On the other hand, when TEMPO is contained in an amount of more than 100 mg per 1 kg of acrylamide, the aqueous acrylamide solution is colored orange, yielding reduced product quality. When manganese ions are contained in an amount of more than 2 mg per 1 kg of acrylamide, there may be an adverse effect on polymerization processes at the time of producing an acrylamide polymer.

Regarding the aqueous acrylamide solution of the present invention, acrylamide concentration is preferably 30 to 60% by mass, more preferably 35 to 55% by mass, and still more preferably 40 to 50% by mass relative to the total weight of the aqueous acrylamide solution.

If the acrylamide concentration is higher than 60% by mass, crystals of acrylamide may easily precipitate near ambient temperature and hence a heating apparatus is required, so that not only facility costs will be increased, but also temperature control and other operations will be complicated. For such reasons, the concentration of the aqueous acrylamide solution of the present invention is, for example, preferably 60% by mass or less, more preferably 55% by mass or less, and most preferably 50% by mass or less, although it is not particularly limited as long as it is within the range where crystals of acrylamide will not precipitate even near ambient temperature.

Meanwhile, if the acrylamide concentration is lower than 30% by mass, it is economically disadvantageous from the industrial standpoint because the tank volume used for storage or keeping will be excessively large or transport costs will also be increased. Thus, the acrylamide concentration in the aqueous acrylamide solution is, for example, preferably 30% by mass or more, more preferably 35% by mass or more, and most preferably 40% by mass or more.

The acrylamide concentration in the aqueous acrylamide solution can be adjusted according to the production condition. For example, for a case in which acrylamide is produced by reacting acrylonitrile with water as described below, it can be adjusted by concentration of acrylonitrile in the raw materials for the reaction, type or shape of the biocatalyst to be used, or the reaction condition (that is, reaction temperature, reaction time, or number of the reactor) or the like.

For the purpose of facilitating stabilization, at least one water soluble monocarboxylic acid salt containing two or more carbon atoms may be contained in the aqueous acrylamide solution of the present invention.

The water soluble monocarboxylic acid salt may be any one of a salt of a saturated monocarboxylic acid or a salt of an unsaturated monocarboxylic acid. Examples of the saturated carboxylic acid include acetic acid, propionic acid, and n-caproic acid. Examples of the unsaturated carboxylic acid include acrylic acid, methacrylic acid, and vinyl acetic acid. Typical salts are sodium salts, potassium salts, and ammonium salts.

Addition amount of the water soluble monocarboxylic acid is preferably an amount which is 20 to 5000 mg as an acid relative to 1 kg of acrylamide.

The aqueous acrylamide solution of the present invention may contain a known stabilizer within a range in which the effect of the present invention is not inhibited.

Examples of the method for producing an aqueous acrylamide solution of the present invention include a method of adding TEMPO and manganese ions to an aqueous acrylamide solution produced by a known method to have a predetermined concentration for each (that is, an aqueous acrylamide solution not containing TEMPO and manganese ions, and hereinbelow, referred to as an "aqueous acrylamide solution as a product"), a method of adding TEMPO and manganese ions to raw materials for the reaction that are used for production of an aqueous acrylamide solution as a product to have a predetermined concentration for each, and a method of adding TEMPO and manganese ions during any process for producing an aqueous acrylamide solution as a product to have a predetermined concentration for each. According to those methods, water soluble monocarboxylic acid salt containing two or more carbon atoms, known stabilizers, or the like may be added to an aqueous acrylamide solution as a product or to the raw materials for the reaction that are used for production of an aqueous acrylamide solution as a product, or they may be added during any process for producing the aqueous acrylamide solution as a product.

Among those described above, from the viewpoint of easiness of controlling concentration of TEMPO and concentration of manganese ions, a method of adding to an aqueous acrylamide solution as a product is preferable.

Method for producing an aqueous acrylamide solution as a product is explained later in detail.

Examples of a method of adding manganese ions include a method of directly adding water soluble manganese salt, a method of dissolving water soluble manganese salt in water and adding a resulting aqueous solution, or the like. Examples of the water soluble manganese salt include manganese sulfate, manganese nitrate, manganese chloride, manganese phosphate, and manganese hydrogen phosphate.

When the addition amount of TEMPO is an extremely small amount relative to the aqueous acrylamide solution as a product, a diluted TEMPO liquid may added for easy addition. Similarly, when the addition amount of manganese ions is an extremely small amount relative to the aqueous acrylamide solution as a product, liquid containing diluted manganese ions may be added for easy addition. At that time, TEMPO and manganese ions may be contained in the same liquid for dilution or a different liquid for dilution. As for the liquid for dilution, water may be used. However, for a case in which a decrease in acrylamide concentration caused by addition of a liquid for dilution is not desirable, it is also possible that the aqueous acrylamide solution as a product with desired acrylamide concentration is used as a liquid for dilution.

In the aqueous acrylamide solution of the present invention, TEMPO and manganese ions are contained in a predetermined amount as described above. However, they exhibit almost no adverse effect on the polymerization (for example, difficulty in obtaining a polymer with desired high molecular weight, decreased polymerization rate, or the like). Thus, the aqueous acrylamide solution obtained by the production method of the present invention can be subjected, while containing TEMPO and manganese ions, to a polymerization process to obtain a desired acrylamide polymer depending on the use thereafter.

(Method for Producing Aqueous Acrylamide Solution as a Product)

The method for producing an aqueous acrylamide solution as a product is not particularly limited, and any known method can be used. In general, a method of reacting acrylonitrile with water to produce acrylamide is preferably used. Examples of the method of reacting acrylonitrile with water include a sulfuric acid hydration process which is the process for earlier industrial production, a copper-catalyzed process which is a current major process for industrial production, and a biocatalyst process which is recently industrialized, and any method can be used.

Among them, a biocatalyst method is preferable in that acrylamide with high purity can be obtained with fewer reaction by-products.

The biocatalyst method is a method of producing acrylamide by reacting acrylonitrile with water in the presence of a biocatalyst, and it is described in many literatures, for example, JP 56-17918 B, JP 59-37951 B, JP 02-470 A, and WO 2009/113654 A. In the present invention, any of those known methods can be used.

Herein, the biocatalyst includes animal cells, plant cells, cell organelles, cell bodies of microorganisms (cell bodies of living or dead microorganisms) or treated products thereof, which contain an enzyme catalyzing a desired reaction (that is, nitrile hydratase).

Such treated products include an enzyme (that is, crude or purified enzyme) extracted from the animal cells, plant cells, cell organelles, cell bodies of microorganisms; or animal cells, plant cells, cell organelles, cell bodies of microorganisms, or enzymes themselves which are immobilized on a carrier; or the like.

Examples of the method for immobilization include entrapping, cross-linking, and carrier binding. Entrapping refers to a technique by which cell bodies of microorganisms or enzymes are enclosed within a fine lattice of polymer gel or coated with a semipermeable polymer membrane. Cross-linking refers to a technique by which enzymes are cross-linked with a reagent having two or more functional groups (that is, a multifunctional cross-linking agent). Furthermore, carrier binding refers to a technique by which enzymes are bound to a water insoluble carrier.

Examples of a carrier (that is, an immobilization carrier) for use in immobilization include glass beads, silica gel, polyurethane, polyacrylamide, polyvinyl alcohol, carrageenan, alginic acid, agar and gelatin.

Cell bodies of microorganisms or treated products thereof are particularly preferable as a biocatalyst.

Examples of the above microorganisms include microorganisms belonging to the genus *Nocardia*, genus *Corynebacterium*, genus *Bacillus*, genus *Pseudomonas*, genus *Micrococcus*, genus *Rhodococcus*, genus *Acinetobacter*, genus *Xanthobacter*, genus *Streptomyces*, genus *Rhizobium*, genus *Klebsiella*, genus *Enterobacter*, genus *Erwinia*, genus *Aeromonas*, genus *Citrobacter*, genus *Achromobacter*, genus *Agrobacterium* and genus *Pseudonocardia*, or the like.

Production of an aqueous acrylamide solution as a product, using a biocatalyst may be carried out by a continuous reaction, by which acrylamide is produced in a continuous manner, or by batch reaction, by which acrylamide is produced in a non-continuous manner. Although not limited thereto, it is preferably carried out by continuous reaction.

When a continuous reaction is carried out, an aqueous acrylamide solution as a product, is produced in a continuous manner without collecting the entire reaction mixture in the reactor while maintaining continuous or intermittent supply of raw materials for reaction (containing a biocatalyst, water as a raw material, and acrylonitrile) to the reactor and continuous or intermittent recovery of the reaction mixture (containing the produced acrylamide) from the reactor.

When a batch reaction is carried out, an aqueous acrylamide solution as a product, is produced by reaction after supplying an entire amount of the raw materials for reaction to the reactor or by reaction with continuous or intermittent supply of remaining part of the raw materials for reaction to the reactor after injecting part of the raw materials for reaction to the reactor.

As for the type of the reactors, reactors of various types such as stirring tank type, fixed bed type, fluid bed type, moving bed type, tubular type, or tower type may be used. Only one reactor may be used or plural reactors may be used in combination. When plural reactors are used in combination, concentration of the recovered acrylamide in a reaction mixture is higher at a downstream side. For such reasons, based on the number of the reactors, concentration of acrylamide in a product, an aqueous acrylamide solution, that is finally obtained can be controlled.

When continuously performing a reaction using plural reactors, the reactor into which the biocatalyst and acrylonitrile are to be supplied is not limited to the most upstream reactor, and the materials may also be introduced into a reactor downstream thereof, as long as it is within a range in which efficiency of the reaction or the like are not impaired too much.

Among the raw materials for reaction, water as a raw material is used for the reaction of acrylonitrile with water for producing acrylamide. Examples of the water as a raw material include water; or an aqueous solution containing acids or salts that are dissolved in water. Examples of the acids include phosphoric acid, acetic acid, citric acid, and boric acid. Examples of the salts include sodium slat, potassium salt, and ammonium salt of the acids. Specific examples of the water as a raw material include, although not particularly limited thereto, pure water, tap water, tris buffer solution, phosphate buffer solution, acetate buffer solution, citrate buffer solution, and borate buffer solution. pH of the water as a raw material is preferably between 5 and 9 (25° C.).

Although the use amount of the biocatalyst may vary depending on the type and form of the biocatalyst to be used, it is preferably adjusted such that the activity of the biocatalyst to be introduced into a reactor is around 50 to 500 U per mg of dried cell bodies of microorganisms at a reaction temperature of 10° C. The above unit "U (unit)" is intended to mean that one micromole of acrylamide is produced for one minute from acrylonitrile, which is measured by using acrylonitrile to be used for production.

Although the use amount of acrylonitrile may vary depending on the type and form of the biocatalyst to be used, it is preferably adjusted such that the acrylonitrile concentration in the raw materials for reaction is around 0.5% to 15.0% by mass with respect to the total mass of the raw materials for reaction.

The reaction temperature (that is, temperature of the reaction mixture) is, although not particularly limited, preferably 10 to 50° C., and more preferably 20 to 40° C. When the reaction temperature is at least 10° C., reaction activity of the biocatalyst can be sufficiently increased. Further, when the reaction temperature is 40° C. or lower, deactivation of the biocatalyst can be easily suppressed.

The reaction time is, although not particularly limited, preferably 1 to 50 hours, and more preferably 3 to 30 hours.

When production of the aqueous acrylamide solution as a product, is carried out by continuous reaction, fluid rate at the time of collecting the reaction mixture from the reactor is determined based on addition rate of acrylonitrile and the biocatalyst such that the production can be made in a continuous manner without collecting the entire reaction mixture in the reactor.

<Stabilizer for Aqueous Acrylamide Solution>

The stabilizer of the present invention is used for stabilization of aqueous acrylamide solution, and it contains TEMPO and manganese ions.

In the stabilizer of the present invention, weight ratio between TEMPO and manganese ions is preferably such that TEMP:manganese ions=2 to 100:0.2 to 2, and more preferably 5 to 50:0.4 to 1.2.

As long as the stabilizing effect of TEMPO and manganese is not lowered, the stabilizer of the present invention may also contain a component other than TEMPO and manganese ions.

Use amount of the stabilizer of the present invention is not particularly limited, and it can be suitably increased or decreased. Preferably, it is an amount such that desired concentration of TEMPO (for example, 2 to 10 mg per 1 kg of acrylamide) and desired concentration of manganese ions (for example, 0.2 to 2 mg per 1 kg of acrylamide) are achieved in an aqueous acrylamide solution added with the corresponding stabilizer.

The stabilizer of the present invention may be used after mixed with other known stabilizer.

<Method for Stabilization of Aqueous Acrylamide Solution>

According to the stabilization method of the present invention, TEMPO is present in the ratio of 2 to 100 mg and manganese ions are present in the ratio of 0.2 to 2.0 mg per 1 kg of acrylamide in the aqueous acrylamide solution. As described above, an aqueous acrylamide solution of a related art (that is, aqueous acrylamide solution as a product) does not contain TEMPO and manganese ions. However, polymerization of acrylamide can be suppressed by including TEMPO and manganese ions at predetermined concentrations, without causing a decrease in quality of an aqueous acrylamide solution or having an adverse effect on polymerization operations. Therefore, stability of the aqueous acrylamide solution can be improved.

Adjustment of the concentration of TEMPO and the concentration of manganese ions can be carried out by addition of TEMPO and manganese, but not limited thereto.

Addition of TEMPO and manganese can be carried out for the aqueous acrylamide solution as a product as described above, for the raw materials for the reaction that are used for production of the aqueous acrylamide solution as a product, or for any process for producing the aqueous acrylamide solution as a product. From the viewpoint of easy adjustment of the concentration of TEMPO and the concentration of manganese ions, addition is made to the aqueous acrylamide solution as a product.

EXAMPLES

The present invention will be further described in more detail by way of the following examples, but the present invention is not limited to them.

Meanwhile, in each example described below, "%" represents "% by mass", unless specifically described otherwise.

As for the pH, values at 25° C. were measured by a glass electrode method.

Example 1

Aqueous Acrylamide Solution Containing 2 mg of TEMPO and 0.2 mg of Manganese Ions Per 1 kg of Acrylamide A 50% aqueous acrylamide solution (pH 6.8, containing 200 mg of acrylic acid per 1 kg of acrylamide, and TEMPO and manganese ions are not contained, hereinbelow, referred to as "aqueous acrylamide solution A") was produced by reacting acrylonitrile with water according to a microbial method. More specifically, according to the method described in Example 2 of JP 2548051 B1, aqueous acrylamide solution A was produced from acrylonitrile.

TEMPO (manufactured by Kanto Chemical Co., Inc.) was diluted with pure water to prepare an aqueous solution of TEMPO in which concentration of TEMPO was 50 mg/kg (hereinbelow, referred to as "50 mg/kg aqueous TEMPO solution").

Manganese sulfate pentahydrate (manufactured by Kanto Chemical Co., Inc.) was diluted with pure water to prepare an aqueous solution of manganese in which concentration of manganese ions was 100 mg/kg (hereinbelow, referred to as "100 mg/kg aqueous manganese solution").

By adding 10.0 g of 50 mg/kg aqueous TEMPO solution and 0.5 g of 100 mg/kg aqueous manganese solution to 500 g of the aqueous acrylamide solution A, an aqueous acrylamide solution containing 2 mg of TEMPO and 0.2 mg of manganese ions per 1 kg of acrylamide was obtained (hereinbelow, referred to as "aqueous acrylamide solution B").

(Evaluation of Appearance of Aqueous Acrylamide Solution)

As a result of observing the appearance of the aqueous acrylamide solution B (that is, presence of absence of coloration) with a naked eye, no coloration was found.

(Evaluation of Stability of Aqueous Acrylamide Solution)

The aqueous acrylamide solution B was taken in an amount of 30 g and introduced into a 50 mL polypropylene container (a product of AS ONE Corporation, under the trade name of Ai-Boy wide-mouth bottle).

A stainless washer (SUS304, inner diameter: 9 mm, outer diameter: 18 mm) was washed with acetone and then with pure water, followed by drying. After drying, the washer was introduced into the 50 mL polypropylene container containing the aqueous acrylamide solution B. This polypropylene container was held in a thermostat kept at 70° C. to measure the number of days required until the acrylamide in the aqueous acrylamide solution B was polymerized (that is, until a pop corn-like polymerized product was produced).

As a result, the pop corn-like polymerized product was produced after 41 days.

Example 2

Aqueous Acrylamide Solution Containing 100 mg of TEMPO and 0.2 mg of Manganese Ions Per 1 kg of Acrylamide By adding 0.025 g of TEMPO and 0.5 g of 100 mg/kg aqueous manganese solution to 500 g of the aqueous acrylamide solution A, an aqueous acrylamide solution containing 100 mg of TEMPO and 0.2 mg of manganese ions per 1 kg of acrylamide was obtained (hereinbelow, referred to as "aqueous acrylamide solution C").

Appearance and stability of the obtained aqueous acrylamide solution C were evaluated in the same order as Example 1. As a result, no coloration was found and a pop corn-like polymerized product was produced after 52 days.

Example 3

Aqueous Acrylamide Solution Containing 2 mg of TEMPO and 2.0 mg of Manganese Ions Per 1 kg of Acrylamide By adding 10.0 g of 50 mg/kg aqueous TEMPO solution and 5.0 g of 100 mg/kg aqueous manganese solution to 500 g of the aqueous acrylamide solution A, an aqueous acrylamide solution containing 2 mg of TEMPO and 2.0 mg of manganese ions per 1 kg of acrylamide was obtained (hereinbelow, referred to as "aqueous acrylamide solution D").

Appearance and stability of the obtained aqueous acrylamide solution D were evaluated in the same order as Example 1. As a result, no coloration was found and a pop corn-like polymerized product was produced after 44 days.

Example 4

Aqueous Acrylamide Solution Containing 100 mg of TEMPO and 2.0 mg of Manganese Ions Per 1 kg of Acrylamide By adding 0.025 g of TEMPO and 5.0 g of 100 mg/kg aqueous manganese solution to 500 g of the aqueous acrylamide solution A, an aqueous acrylamide solution containing 100 mg of TEMPO and 2.0 mg of manganese ions per 1 kg of acrylamide was obtained (hereinbelow, referred to as "aqueous acrylamide solution E").

Appearance and stability of the obtained aqueous acrylamide solution E were evaluated in the same order as Example 1. As a result, no coloration was found and a pop corn-like polymerized product was produced after 53 days.

Comparative Example 1

Aqueous Acrylamide Solution not Added with TEMPO and Manganese Ions

Appearance and stability of the aqueous acrylamide solution A were evaluated in the same order as Example 1. As a result, no coloration was found but a pop corn-like polymerized product was produced after 3 days.

Comparative Example 2

Aqueous Acrylamide Solution Containing 1 mg of TEMPO and 0.1 mg of Manganese Ions Per 1 kg of Acrylamide By adding 5.0 g of 50 mg/kg aqueous TEMPO solution and 0.25 g of 100 mg/kg aqueous manganese solution to 500 g of the aqueous acrylamide solution A, an aqueous acrylamide solution containing 1 mg of TEMPO and 0.1 mg of manganese ions per 1 kg of acrylamide was obtained (hereinbelow, referred to as "aqueous acrylamide solution F").

Appearance and stability of the obtained aqueous acrylamide solution F were evaluated in the same order as Example 1. As a result, no coloration was found but a pop corn-like polymerized product was produced after 6 days.

Comparative Example 3

Aqueous Acrylamide Solution Containing 1 mg of TEMPO and 3.0 mg of Manganese Ions Per 1 kg of Acrylamide By adding 5.0 g of 50 mg/kg aqueous TEMPO solution and 7.5 g of 100 mg/kg aqueous manganese solution to 500 g of the aqueous acrylamide solution A, an aqueous acrylamide solution containing 1 mg of TEMPO and 3.0 mg of manganese ions per 1 kg of acrylamide was obtained (hereinbelow, referred to as "aqueous acrylamide solution G").

Appearance and stability of the obtained aqueous acrylamide solution G were evaluated in the same order as Example 1. As a result, no coloration was found but a pop corn-like polymerized product was produced after 8 days.

Comparative Example 4

Aqueous Acrylamide Solution Containing 150 mg of TEMPO and 0.1 mg of Manganese Ions Per 1 kg of Acrylamide By adding 0.0375 g of TEMPO and 0.25 g of 100 mg/kg aqueous manganese solution to 500 g of the aqueous acrylamide solution A, an aqueous acrylamide solution containing 150 mg of TEMPO and 0.1 mg of manganese ions per 1 kg of acrylamide was obtained (hereinbelow, referred to as "aqueous acrylamide solution H").

Appearance and stability of the obtained aqueous acrylamide solution H were evaluated in the same order as Example 1. As a result, it was colored orange and a pop corn-like polymerized product was produced after 31 days.

Comparative Example 5

Aqueous Acrylamide Solution Containing 2 mg of TEMPO and 0.1 mg of Manganese Ions Per 1 kg of Acrylamide By adding 10.0 g of 50 mg/kg aqueous TEMPO solution and 0.25 g of 100 mg/kg aqueous manganese solution to 500 g of the aqueous acrylamide solution A, an aqueous acrylamide solution containing 2 mg of TEMPO and 0.1 mg of manganese ions per 1 kg of acrylamide was obtained (hereinbelow, referred to as "aqueous acrylamide solution I").

Appearance and stability of the obtained aqueous acrylamide solution I were evaluated in the same order as Example 1. As a result, no coloration was found but a pop corn-like polymerized product was produced after 9 days.

Comparative Example 6

Aqueous Acrylamide Solution Containing 1 mg of TEMPO and 0.2 mg of Manganese Ions Per 1 kg of Acrylamide By adding 5.0 g of 50 mg/kg aqueous TEMPO solution and 0.5 g of 100 mg/kg aqueous manganese solution to 500 g of the aqueous acrylamide solution A, an aqueous acrylamide solution containing 1 mg of TEMPO and 0.2 mg of manganese ions per 1 kg of acrylamide was obtained (hereinbelow, referred to as "aqueous acrylamide solution J").

Appearance and stability of the obtained aqueous acrylamide solution J were evaluated in the same order as Example 1. As a result, no coloration was found but a pop corn-like polymerized product was produced after 5 days.

TABLE 1

|  | Concentration of TEMPO [mg/kg] (relative to acrylamide) | Concentration of manganese ions [mg/kg] (relative to acrylamide) | Number of days required for polymerization [Days] | Coloration of aqueous acrylamide solution |
| --- | --- | --- | --- | --- |
| Example 1 | 2 | 0.2 | 41 | None |
| Example 2 | 100 | 0.2 | 52 | None |
| Example 3 | 2 | 2.0 | 44 | None |
| Example 4 | 100 | 2.0 | 53 | None |
| Comparative example 1 | 0 | 0 | 3 | None |
| Comparative example 2 | 1 | 0.1 | 6 | None |
| Comparative example 3 | 1 | 3 | 8 | None |
| Comparative example 4 | 150 | 0.1 | 31 | Colored orange |
| Comparative example 5 | 2 | 0.1 | 9 | None |
| Comparative example 6 | 1 | 0.2 | 5 | None |

As described in the above results, by containing TEMPO in the ratio of 2 to 100 mg and manganese ions in the ratio of 0.2 to 2.0 mg per 1 kg of acrylamide in an aqueous acrylamide solution, polymerization of the acrylamide can be suppressed without lowering quality of the acrylamide so that the stability of the aqueous acrylamide solution can be significantly improved.

INDUSTRIAL APPLICABILITY

According to the present invention, an aqueous acrylamide solution can be conveniently stabilized without lowering quality of acrylamide. Therefore, the present invention is useful as a method for preventing polymerization of acrylamide during production, storage and/or transport of the aqueous acrylamide solution.

The invention claimed is:

1. An aqueous acrylamide solution, comprising:
   acrylamide;
   2,2,6,6-tetramethylpiperidine 1-oxyl in an amount of 2 to 100 mg per kg of acrylamide;
   manganese ions in an amount of 0.2 to 2.0 mg per kg of acrylamide; and
   a water soluble monocarboxylic acid salt containing two or more carbon atoms added in an amount of 20 to 5000 mg per kg of acrylamide.

2. The aqueous acrylamide solution according to claim 1, wherein the acrylamide is obtained by a process comprising: reacting acrylonitrile with water in the presence of a biocatalyst.

3. The aqueous acrylamide solution according to claim 1, wherein a concentration of the acrylamide in the aqueous acrylamide solution is from 30 to 60% by mass relative to a total weight of the aqueous acrylamide solution.

4. A stabilizer for an aqueous acrylamide solution, the stabilizer comprising:
   2,2,6,6-tetramethylpiperidine 1-oxyl;
   manganese ions; and
   a water soluble monocarboxylic acid salt containing two or more carbon atoms;
   wherein the water soluble monocarboxylic acid salt is present in the stabilizer in an amount sufficient to provide 20 to 5,000 mg per kg of acrylamide when the stabilizer is added to the aqueous acrylamide solution.

5. A method for stabilizing an aqueous acrylamide solution, the method comprising:
   mixing 2,2,6,6-tetramethylpiperidine 1-oxyl and manganese ions into the aqueous acrylamide solution in amounts of 2 to 100 mg of 2,2,6,6-tetramethylpiperidine 1-oxyl per kg acrylamide and 0.2 to 2.0 mg of manganese ions per kg of acrylamide; and
   adding a water soluble monocarboxylic acid salt containing two or more carbon atoms to the aqueous acrylamide solution in an amount of 20 to 5,000 mg per kg of acrylamide.

6. A method for stabilizing an aqueous acrylamide solution, the method comprising:
   adding a composition comprising 2,2,6,6-tetramethylpiperidine 1-oxyl and manganese ions to the aqueous acrylamide solution; and
   further adding a water soluble monocarboxylic acid salt containing two or more carbon atoms to the aqueous acrylamide solution;
   wherein the water soluble monocarboxylic acid salt is added in an amount of 20 to 5,000 mg per kg of acrylamide.

7. The aqueous acrylamide solution according to claim 1, wherein the water soluble monocarboxylic acid salt is a salt of acetic acid, propionic acid, or n-caproic acid.

8. The aqueous acrylamide solution according to claim 1, wherein the water soluble monocarboxylic acid salt is a salt of acrylic acid, methacrylic acid, or vinyl acetic acid.

9. The aqueous acrylamide solution according to claim 1, wherein the water soluble monocarboxylic acid salt is a sodium salt, potassium salt, or ammonium salt of a monocarboxylic acid.

10. The stabilizer according to claim 4, wherein the water soluble monocarboxylic acid salt is a salt of acetic acid, propionic acid, or n-caproic acid.

11. The stabilizer according to claim 4, wherein the water soluble monocarboxylic acid salt is a salt of acrylic acid, methacrylic acid, or vinyl acetic acid.

12. The stabilizer according to claim 4, wherein the water soluble monocarboxylic acid salt is a sodium salt, potassium salt, or ammonium salt of a monocarboxylic acid.

13. The method according to claim 5, wherein the water soluble monocarboxylic acid salt is a salt of acetic acid, propionic acid, or n-caproic acid.

14. The method according to claim 5, wherein the water soluble monocarboxylic acid salt is a salt of acrylic acid, methacrylic acid, or vinyl acetic acid.

15. The method according to claim 5, wherein the water soluble monocarboxylic acid salt is a sodium salt, potassium salt, or ammonium salt of a monocarboxylic acid.

16. The method according to claim 6, wherein the water soluble monocarboxylic acid salt is a salt of acetic acid, propionic acid, or n-caproic acid.

17. The method according to claim 6, wherein the water soluble monocarboxylic acid salt is a salt of acrylic acid, methacrylic acid, or vinyl acetic acid.

18. The method according to claim 6, wherein the water soluble monocarboxylic acid salt is a sodium salt, potassium salt, or ammonium salt of a monocarboxylic acid.

\* \* \* \* \*